United States Patent [19]

Marshall

[11] Patent Number: 4,530,900

[45] Date of Patent: Jul. 23, 1985

[54] SOLUBLE INSOLUBLE POLYMERS IN ENZYMEIMMUNOASSAY

[75] Inventor: David L. Marshall, Carmel, Ind.

[73] Assignee: Seragen Diagnostics Inc., Indianapolis, Ind.

[21] Appl. No.: 417,281

[22] Filed: Sep. 13, 1982

[51] Int. Cl.³ .................. G01N 33/54; C12N 9/96
[52] U.S. Cl. .................................. 435/7; 435/188; 436/536; 436/538; 436/539; 436/540; 436/815; 436/824; 436/828
[58] Field of Search ............ 435/4, 7, 188, 178; 436/518, 529, 531, 536, 538, 539, 540, 816, 824, 828, 815

[56] References Cited

U.S. PATENT DOCUMENTS

| 3,791,932 | 2/1977 | Schuurs et al. | 435/7 |
| 3,850,752 | 11/1974 | Schuurs et al. | 435/7 |
| 4,003,792 | 1/1977 | Mill et al. | |
| 4,134,792 | 1/1979 | Boquslaski et al. | 435/7 |
| 4,233,401 | 11/1980 | Yoshida et al. | 435/7 |
| 4,238,565 | 12/1980 | Hornby et al. | 435/7 |
| 4,289,747 | 9/1981 | Chu | 435/7 |
| 4,298,685 | 11/1981 | Parikh et al. | 435/7 |
| 4,352,883 | 10/1982 | Lim | 435/178 |
| 4,371,515 | 2/1983 | Chu | 435/7 |
| 4,407,957 | 10/1983 | Lim | 435/178 |

FOREIGN PATENT DOCUMENTS 57-7557  1/1982  Japan ..................... 435/7

OTHER PUBLICATIONS

M. Charles, R. W. Coughlin and F. X. Hasselberger, *Biotechnology and Bioengineering*, vol. XVI, pp. 1153–1156, (1974).
A. L. Margolin et al., *Biotechnology and Bioengineering*, vol. XXIV, pp. 237–240, (1982).
D. Worl et al., *Clin. Chem.*, 27(5), 673–677, (1981).
That. T. Ngo et al., *J. Immunological Methods*, 42, 93–103, (1981).
A. J. O'Brierne and H. R. Cooper, *J. Hist. Cytochemistry*, 27(8), 1148–1162, (1979).

*Primary Examiner*—Esther M. Kepplinger
*Attorney, Agent, or Firm*—Paul J. Cook; Stephen L. Nesbitt

[57] ABSTRACT

The invention pertains to an improved heterogeneous enzymeimmunoassay involving the use of a reversibly soluble polymeric substance acting as the support for the antibody. In the direct method the antigen to be detected and an enzyme labeled antigen are bound by antibody which is chemically linked to the soluble polymeric substance. The polymer is rendered insoluble and removed from the test solution. After resolubilization into a solution containing substrate for the enzyme label, the assay for antigen is completed by determination of enzymatic activity. In the indirect method, the antigen to be detected and an enzyme labeled antigen are incubated with a primary antibody unattached to the polymeric substance. After addition of a second antibody which is chemically linked to the polymeric substance, the polymer is rendered insoluble and the assay is performed as in the direct method described above.

11 Claims, No Drawings

SOLUBLE INSOLUBLE POLYMERS IN ENZYMEIMMUNOASSAY

BACKGROUND OF THE INVENTION

Enzymeimmunoassay (EIA) has gained increasing importance as an analytical procedure during the last decade or so. These techniques combine the inherent sensitivity of the antigen-antibody reaction with the advantages of conventional enzymatic analysis. Representative descriptions of prior art EIA may be found in U.S. Pat. Nos. 4,134,792, 4,238,565 and 3,791,932 and in D. Woral et. al., *Clin. Chem.* 27(5), 673–677 (1981), That. T. Ngo et. al., *J. Immunological Methods* 42, 93–103 (1981) and A. J. O'Beirne and H. R. Cooper, *J. Hist. Cytochemistry*, 27(8), 1148–1162 (1979).

EIA is generally categorized into two major classes, homogeneous and heterogeneous enzymeimmunoassays. In homogeneous EIA, all the components are soluble in the test solution and are not separated prior to enzymatic activity determination. In heterogeneous EIA, either a solid phase component is utilized which allows the separation of bound from unbound components or a component of the initial solution is caused to precipitate and is subsequently removed from the solution. Such precipitation by prior art procedures is irreversible. In the prior art, kinetic enzyme analysis of the separated solid phase or precipitate was largely impractical due to limitations of solid phase reactions.

SUMMARY OF THE INVENTION

Applicant has discovered that attachment of the antibody to a soluble polymeric substance which can be rendered reversibly insoluble, allows for the enzymatic assay of the solid phase in heterogeneous EIA, a variation of enzymeimmunoassay not previously feasible. In the presently contemplated assay, antibody is chemically linked to a polymeric substance, which can be rendered soluble or insoluble under conditions which do not affect the ability of antibody to bind antigen and which do not affect the activity of the enzyme label. While in the soluble form, the antibody-polymeric substance conjugate is allowed to react with a solution containing the unknown and enzyme labeled unknown. The polymer is then rendered insoluble, removed from the solution of unknown and subsequently resolubilized in a solution containing enzyme substrate. The rate of substrate conversion, which is related to the quantity of unknown in the initial solution, is determined by well known technology. By virtue of being in soluble form, the enzyme analysis step can be determined in a variety of automated clinical analyzers.

PREFERRED EMBODIMENTS

The EIA of the present invention can be performed either by the direct or indirect methods. In the direct method, the soluble antibody-polymeric substance conjugate is allowed to react with a known quantity of antigen-enzyme conjugate and an unknown quantity of antigen in a test solution. The antibody-polymeric substance conjugate binds antigen or antigen-enzyme conjugate in amounts which is related to the relative quantities of antigen and antigen-enzyme conjugate present. The antibody-polymeric substance conjugate having antigen or antigen-enzyme conjugate attached thereto is then rendered insoluble and physically removed from the test solution by, for example, filtration or centrifugation. The insoluble polymeric substance is then resolubilized and any enzyme attached thereto is allowed to react with the appropriate enzyme substrate. The conversion of substrate to product is monitored in any manner known for monitoring the enzyme reaction such as by photometric analysis used in traditional enzymatic analysis or in conventional EIA. The rate of the enzyme reaction is proportional to the amount of antigen in the initial test solution. As in traditional enzymatic analysis, it is advisable to concurrently perform the analytical procedure employing a test solution having a known quantity of antigen present and comparing the results thereto in order to appropriately compensate for the variability of results inherent in such a procedure.

Where the close proximity of the polymeric substance might substantially impair the ability of the attached primary antibody to bind antigen, the indirect method should be utilized. In this procedure, a "binding agent", rather than the primary antibody, is bound to the polymeric substance. The binding agent can be either a second antibody (an antibody directed against the primary antibody), protein A or avidin. Where the binding agent is avidin, the primary antibody is "labeled" with biotin. The primary antibody is allowed to bind antigen and antigen-enzyme conjugate in the test solution. The resulting complex is then allowed to react with the binding agent-polymeric substance conjugate. Where the binding agent is a second antibody, the immunological complex of the primary and second antibodies results and where the binding agent is avidin, a complex with the biotin label of the primary antibody results. The binding agent-polymeric substance conjugate having primary antibody and either antigen or antigen-enzyme conjugate attached thereto is then rendered insoluble and a procedure analogous to that of the direct method described above is followed.

Antigen, as used herein, is the substance whose presence and quantity is to be determined. The antigen can be any substance for which there exists a naturally occurring antibody or for which an antibody can be prepared. Antigen, as used herein, includes haptens, those substances which are, of themselves, incapable of eliciting antibody formation unless attached to an antigenic carrier substance such as protein. The antigen can be, for example, a protein, a peptide such as enkephalin, an amino acid such as histidine, a steroid such as estrogen, an alkaloid such as morphine, a vitamin such as folic acid, a hormone such as thyroxine, a drug including those therapeutically administered as well as those administered for illicit purposes, a metabolite such as uric acid and antibodies to any of these above substances. Generally speaking the antigen can have a molecular weight of from 50 to 1,000,000 or greater, preferably from 100 to 50,000. Examples of antigens which can be assayed by the present scheme are theophylline, human chorionic gonadotropin (HCG), heroin, phenobarbital, digoxin, testosterone, aspirin or folic acid. The antigen of the antigenenzyme conjugate can be the antigen or an immunological analog thereof, that is, a substance which is a simple chemical derivative of the antigen and which is recognized by the antibody.

Suitable polymeric substances for use in the present assay system are any naturally occurring or synthetically prepared material which can be rendered soluble or insoluble depending on conditions employed and to which the required antibody or binding agent may be chemically attached without significantly impairing the ability of the antibody to bind antigen or of the binding agent to bind its partner. Preferably the ability of antibody to bind antigen or of the binding agent to bind its partner, after attachment to the polymeric substance, would be at least 25% of the value of the free antibody or binding agent, more preferably at least 75% and most preferably at least 90%. Ideally, attachment of the antibody or binding agent to the polymeric substance would result in no diminution of the ability of antibody to bind antigen or of the binding agent to bind its partner. For example, any natural or synthetic polymer having free carboxyl groups is capable of forming water soluble sodium salts and water insoluble calcium salts. Alginic acid, a carbohydrate obtained by alkaline extraction of various species of seaweed; pectin, a polysaccharide substance derived chiefly from citrus fruit; pectic acid, a partially synthetic polymer prepared by alkaline treatment of pectin; celluronic acid, a synthetic polymer of glucuronic acid and glucose; carrageenan, a polysaccharide mucilage formed primarily from certain species of red algae; ethylene-maleic anhydride copolymer, a synthetic polymer prepared by reaction of ethylene and maleic anhydride; carboxymethylcellulose, a synthetic polymer derived from cellulose; and, polyacrylic acid, a polymer of acrylic acid, are exemplary polymeric substances. These substances are readily water soluble but may be rendered insoluble, for example, by lowering the pH of the solution or by the addition of certain metal ions such calcium ion. The insolubilized polymeric substance may be resolubilized by raising the pH of the solution or by the addition of metal chelating agents such as citrate ion or ethylenediaminetetraacetic acid (EDTA). Alginic acid is the preferred polymeric substance. A further discussion of suitable polymeric substances can be found in U.S. Pat. No. 4,003,792.

The primary antibody in the present scheme, is the immunological mate to the antigen. The antibody may be naturally occurring or may be prepared by conventional techniques, such as by introduction of the antigen into the serum of an animal and subsequently isolating the appropriate immunoglobulin fraction.

The antibody can be attached to the polymeric substance to form the antibody-polymeric substance conjugate in any manner which preserves the ability of the antibody to bind antigen in the subsequent analytical scheme. Where alginic acid is the polymeric substance, the antibody can be attached to the alginic acid by, for example, activating the alginic acid by reaction with either cyanogen bromide or a carbodiimide reagent such as dicyclohexylcarbodiimide or 1-ethyl-3-(3-dimethylamino-propyl) carbodiimide, and subsequently reacting the activated alginic acid with the antibody. In a like manner, the binding agent (a second antibody, protein A or avidin) can be attached to the polymeric substance to form the binding agent-polymeric substance conjugate. Other methods of attaching the antibody to the polymeric substance are well known in the prior art, for example, in U.S. Pat. No. 4,003,792.

The enzyme label chosen for use in the present analytical scheme can be any enzyme, preferably an enzyme whose activity can be conveniently monitored by, for example, spectrophotometric observation of the conversion of enzyme substrate to product directly or by a secondary reaction where a colored substance appears or disappears. Where, for example, glucose oxidase is the enzyme and glucose is the substrate, the rate of the reaction may be followed by the appearance of a colored product formed in a secondary reaction involving the hydrogen peroxide formed in the reaction of glucose with the enzyme. Moreover, the conditions utilized to precipitate and subsequently resolubilize the polymeric substance should not significantly alter the ability of the enzyme label to convert the substrate to product. Further, the enzyme when chemically bonded to the antigen or an immunological analog thereof to form the antigen-enzyme conjugate, should not suffer significantly impaired ability to convert substrate to product. Preferably the enzymatic activity of the enzyme in the antigen-enzyme conjugate after precipition and resolubilization would be at least 25% of the ability of free enzyme to act on substrate, more preferably at least 75%, most preferably at least 90%. Ideally, bonding to antigen, precipitation and resolubilization would result in no diminution of the enzymatic activity.

The enzyme can be chemically bonded to the antigen or immunological analog thereof in any manner to form the antigen-enzyme conjugate. In general, attachment of enzyme to antigen employs substituents present in the enzyme and antigen such as hydroxyl, amino, carboxyl or keto groups and may also employ a bifunctional linking group. If desirable, the linking group can be of varying length in order to spatially separate the enzyme and antigen of the antigen-enzyme conjugate. Such methods as utilized in prior art EIA are discussed in, for example, U.S. Pat. Nos. 4,233,401, 3,850,752 and 4,134,792.

The test solution can be any naturally occurring or otherwise derived solution suspected of containing the antigen. Suitable test solutions of a biological nature are, for example, blood serum or plasma, lymphatic fluid, cerebrospinal fluid, amniotic fluid, saliva or urine.

The biotin label of the primary antibody required of the indirect method when the binding agent is avidin can be accomplished in any manner consistent with substantially maintaining the ability of the primary antibody to bind antigen or antigen-enzyme conjugate. Preferably, the biotin label is chemically attached to the antibody by reaction of the primary antibody with the N-hydroxysuccinimide ester derivative of biotin.

The following examples are illustrative of the Applicant's invention but should not be deemed to, in any way, limit the scope of the invention.

EXAMPLE 1

Alginic Acid Activation-Cyanogen Bromide Method

Sodium alginate was dissolved in water to make a 1% solution. To 1.0 ml alginate solution was added 1.0 ml of pH 10.7 $NaHCO_3/Na_2CO_3$ solution followed by addition of 5 mg solid cyanogen bromide. After mixing for 30 minutes at room temperature, the solution was dialyzed for 2 hours against water at pH 9 to yield the activated alginic acid.

EXAMPLE 2

Alginic Acid Activation-Carbodiimide Method

One (1) ml of 0.5% Aqueous sodium alginate was adjusted to pH 4.7. Five (5) mg 1-Ethyl-3-(3-dimethylaminopropyl) carbodiimide was added and allowed to react for 10 minutes to produce the activated alginic acid.

EXAMPLE 3

Preparation of Antibody-Alginic Acid And Binding Agent-Alginic Acid Conjugates To 1 ml of the activated alginic acid prepared in Example 1 or 2 above, was added 1 ml of a solution of (a) the IgG fraction from a rabbit antitheophylline serum purification (Example 4), (b) the IgG fraction of a goat antirabbit IgG serum (Pel-Freez), (c) protein A (Pharmacia), or (d) avidin (Sigma). The protein concentration was 0.5–1.0 mg/ml. After allowing the solutions to stand at 4° C. overnight, the protein-alginic acid conjugate was precipitated by adding 3 ml of a 1% calcium chloride solution. The precipitate was washed with water and then resolubilized by the addition of a solution of 2 ml tris-(hydroxymethyl)-aminomethane (TRIS) and a sufficient amount of 0.4 M sodium citrate, pH 6.3, to completely dissolve the alginic acid. In this manner (a) rabbit antitheophylline IgG-alginic acid conjugate, (b) goat antirabbit IgG-alginic acid conjugate, (c) protein A-alginic acid conjugate, and (d) avidin-alginic acid conjugate, respectively, were prepared.

EXAMPLE 4

Purification of The IgG Fraction of Theophylline Antiserum

One (1) ml rabbit antitheophylline serum (Western Chemical Research Corporation) was placed into a column packed with 5 ml protein A-sepharose ge (Pharmacia) which had equilibrated with 0.02 M phosphate at pH 7.5. After washing through all the non-bound material, the IgG fraction was eluted with 6 ml 0.58% acetic acid and collected in a bottle containing 4 ml borate buffer at pH 9.0. The product was used to prepare the antitheophylline IgG-alginic acid conjugate in Example 3 and to prepare the biotin-antitheophylline IgG conjugate in Example 5.

EXAMPLE 5

Biotin Labeling of IgG

To 1 ml of the IgG solution prepared in Example 4, there was added 8 mg of sodium bicarbonate followed by 0.05 ml of Biotin-N-hydroxysuccinimide (Pierce) in dimethylformamide (1.5 mg/0.05 ml). After 1 hour at room temperature, the solution was dialyzed overnight at 4° C. against 0.02M phosphate, pH 7, containing 0.15M sodium chloride to produce the Biotin-IgG conjugate.

EXAMPLE 6

Theophylline Enzyme Immunoassay Direct Method

The antitheophylline-alginate conjugate from Example 3 was diluted with 0.5% sodium alginate and the various dilutions allowed to react with theophylline-alkaline phosphatase conjugate (Immunotech). Using a dilution which gives 50–60% binding of the theophylline-alkaline phosphatase, a dose-response curve was produced by the following assay procedure: Add 0.02 ml theophylline serum standards to numbered plastic tubes followed by 0.2 ml theophylline-alkaline phosphatase. Then, 0.2 ml of antitheophylline-alkaline conjugate was added to each tube and each tube vortexed. After a 30 minute, 37° C. incubation, the alginate was rendered insoluble by addition of 2 ml of 1% $CaCl_2$. The tubes were centrifuged and the supernatants were discarded. To the pellet in each tube was added 1 ml p-nitrophenyl phosphate solution (1 mg/ml in pH 10 bicarbonate buffer). The color which is produced can be measured kinetically since the pellet is resolubilized by addition of the substrate buffer, or stopping solution can be added (0.2 N NaOH) if the color is to be measured in a manual approach.

Indirect Method

The same assay protocol described above in Example 6 was followed except that the antitheophylline serum was used in an unmodified form (also diluted to produce 50–60% binding of enzyme-conjugate during the assay). After the incubation of standard theophylline-alkaline phosphatase conjugate and antitheophylline antibody, 0.05 ml of goat antirabbit IgG-alginic acid conjugate from Example 3 was added to each tube. Following a short incubation of 1–2 minutes, the polymer was rendered insoluble by addition of 2 ml of 1% $CaCl_2$. The rest of the procedure is identical to the direct method described above.

Results from each dose-response assay are shown in Table 1. The absorbance values for the indirect assay are higher than the direct method because more theophylline-alkaline phosphatase was used. However, each method shows the expected response from a competitive binding immunoassay.

TABLE 1

| Comparison of the theophylline dose response obtained by the Direct and Indirect Methods. Absorbance (405 nm) | | |
|---|---|---|
| Theophylline Standard | Direct Assay | Indirect Assay |
| 1 μg/ml | 0.92 | 1.34 |
| 4 μg/ml | 0.63 | 1.05 |
| 10 μg/ml | 0.43 | 0.87 |
| 20 μg/ml | 0.34 | 0.67 |
| 40 μg/ml | 0.28 | 0.49 |

I claim:

1. A method for determining the presence of a soluble antigen in a test solution which comprises in sequence:
   (a) allowing a soluble antibody-polymeric substance conjugate to react with the soluble antigen and a soluble antigen-enzyme conjugate in the test solution, said antibody being the reactive complement to said soluble antigen and to the antigen moiety of the antigen-enzyme conjugate thereby to form a reaction product containing said polymeric substance;
   (b) causing the reaction product containing the polymeric substance to precipitate and separating the solid formed thereby from the test solution;
   (c) resolubilizing the reaction product containing the polymeric substance to form a second test solution;
   (d) adding a substrate for the enzyme to said second test solution; and
   (e) measuring the enzymatic activity in the second test solution compared to the enzymatic activity in a medium derived from a solution having a known amount of antigen.

2. A method of claim 1 wherein the polymeric substance is alginic acid.

3. A method of claim 2 wherein the polymeric substance is rendered insoluble by the addition of calcium ion.

4. A method of claim 2 wherein the antigen is theophylline.

5. A method for determining the presence of a soluble antigen in a test solution which comprises in sequence:

(a) allowing a primary antibody to react with the soluble antigen and a soluble antigen-enzyme conjugate in the test solution, said antibody being the reactive complement to said soluble antigen and to the antigen moiety of the antigen-enzyme conjugate thereby to form a first reaction product containing said primary antibody and said antigen and a second reaction product containing said primary antibody and said antigen-enzyme conjugate;

(b) adding a binding agent-polymeric substance conjugate to the resulting solution, said binding agent being capable of binding to said primary antibody and said polymer substance without hindering the ability of the primary antibody to react with the antigen-enzyme conjugate thereby to form a third reaction product containing said polymeric substance;

(c) causing the third reaction product containing said polymeric substance to precipitate and separating the solid formed thereby from the test solution;

(d) resolubilizing the third reaction product containing said polymeric substance to form a second test solution;

(e) adding a substrate for the enzyme to said second test solution; and (f) measuring the enzymatic activity in the second test solution compared to the enzymatic activity in a medium derived from a solution having a known amount of antigen.

6. A method of claim 5 wherein the polymeric substance is alginic acid or ethylene-maleic anhydride copolymer.

7. A method of claim 5 wherein the polymeric substance is rendered insoluble by the addition of calcium ion.

8. A method of claim 5 wherein the binding agent is avidin or protein A.

9. A method of claim 5 wherein the binding agent is a second antibody with specificity for the primary antibody.

10. A method of claim 5 wherein the antigen is theophylline.

11. A method of claim 8 wherein the binding agent is avidin and the primary antibody is labeled with biotin.

* * * * *